US010107940B2

(12) United States Patent
Yu et al.

(10) Patent No.: US 10,107,940 B2
(45) Date of Patent: Oct. 23, 2018

(54) SMALL-SCALE LIGHT ABSORBERS WITH LARGE ABSORPTION CROSS-SECTIONS

(71) Applicant: Wisconsin Alumni Research Foundation, Madison, WI (US)

(72) Inventors: Zongfu Yu, Madison, WI (US); Ming Zhou, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 263 days.

(21) Appl. No.: 14/885,359

(22) Filed: Oct. 16, 2015

(65) Prior Publication Data

US 2017/0108620 A1 Apr. 20, 2017

(51) Int. Cl.
*G02B 1/00* (2006.01)
*G02B 17/00* (2006.01)
*G02B 21/08* (2006.01)
*G02B 21/00* (2006.01)
*G01N 21/64* (2006.01)

(52) U.S. Cl.
CPC ......... *G02B 1/007* (2013.01); *G01N 21/6428* (2013.01); *G01N 21/6458* (2013.01); *G02B 17/002* (2013.01); *G02B 21/0064* (2013.01); *G02B 21/08* (2013.01); *G01N 2021/6439* (2013.01); *G01N 2021/6478* (2013.01)

(58) Field of Classification Search
CPC .... G02B 1/007; G02B 21/0064; G02B 21/08; G02B 17/002; G01N 21/6458; G01N 21/6428; G01N 2021/6478; G01N 2021/6439
USPC ........................................... 250/459.1, 458.1
See application file for complete search history.

(56) References Cited

U.S. PATENT DOCUMENTS

| | | | |
|---|---|---|---|
| 2004/0095658 A1* | 5/2004 | Buretea | B82Y 20/00 359/853 |
| 2008/0212866 A1* | 9/2008 | Lett | G01N 21/6428 382/133 |
| 2013/0292788 A1* | 11/2013 | Coimbatore Balram | H01L 31/0352 257/443 |
| 2017/0097558 A1* | 4/2017 | Belkin | G02F 1/3556 |
| 2017/0288079 A1* | 10/2017 | Schubert | H01L 31/055 |

OTHER PUBLICATIONS

Ming Zhou et al.: "Extraordmarily Large Optical Cross Section for Localized Single Nanoresonator." Physical review letters 115, No. 2 (Jul. 2015): pp. 023903-1 thru 023903-5: USA.
Ruben Maas et al.:"Experimental realization of an epsilon-near-zero metamaterial at visible wavelengths." Nature Photonics vol. 7, No. 11: Macmillan Publishers Limited; (Nov. 2013): pp. 907-912, USA.
Parikshit Moitra et al. "Realization of an all-dielectric zero-index optical metamaterial," Nature Photonics vol. 7, No. 10 (Oct. 2013): pp. 791-795: USA.
Xueqin Huang et al.; "Dirac cones induced by accidental degeneracy in photonic crystals and zero-refractive-index materials." Nature materials; vol. 10, No. (Aug. 2011). pp. 582-586; USA.

* cited by examiner

*Primary Examiner* — David Porta
*Assistant Examiner* — Gisselle Gutierrez
(74) *Attorney, Agent, or Firm* — Boyle Fredrickson, S.C.

(57) ABSTRACT

A resonator coupled to a system exhibiting a negative phase index of refraction presents a magnified absorption cross-section providing an optical element that can be used for enhancing taggant detection or increasing photodetector efficiency.

17 Claims, 3 Drawing Sheets

SMALL-SCALE LIGHT ABSORBERS WITH LARGE ABSORPTION CROSS-SECTIONS

STATEMENT REGARDING FEDERALLY SPONSORED RESEARCH OR DEVELOPMENT

This invention was made with government support under N00014-14-1-0300 awarded by the US Navy/ONR. The government has certain rights in the invention.

CROSS REFERENCE TO RELATED APPLICATION

--

BACKGROUND OF THE INVENTION

The present invention relates to structures for processing electromagnetic radiation and in particular to a structure that greatly increases the absorption cross-section of small electromagnetic resonators.

Concentrating the light received by an optical device or other device for processing electromagnetic radiation can be important in increasing the effectiveness of the device. For example, the electrical signal obtainable from a radiation detector such as an antenna or photodetector can be increased by increasing the concentration of light received by the detector. Similarly, the ability to detect a radiation taggant, for example, a nanoresonator, is improved by increasing the concentration of light onto the taggant effectively increasing the area over which radiation is absorbed.

Conventional concentrators used for optical systems, such as lenses, are limited in effectiveness for extremely small optical devices such as nanoresonators. For example, the "absorption cross-section" $\sigma_0$ of a nanoresonator with an isotropic angular response having a resonant wavelength of $\lambda_0$ is:

$$\sigma_0 = \lambda_0^2/4\pi \tag{1}$$

As a result, generally as the size of the nanoresonator decreases, so does the size of its resonant wavelength and accordingly its absorption cross-section, greatly limiting the energy that can be coupled into the nanoresonator.

Some techniques have been developed to increase the size of the absorption cross-section of the nanoresonator but generally these increases have been less than $10\sigma_0$.

SUMMARY OF THE INVENTION

The present invention provides a way of greatly increasing the absorption cross-section of a nanoresonator or other resonator well in excess of $10\sigma_0$. The technique associates the material having low "phase index of refraction", for example, less than 0.1, radically increasing the absorption cross-section many times over the previous limits, for example, as much as or greater than $1000\sigma_0$.

Unlike a conventional lens type concentrator, the invention expands the area of the light coupled to the optical device without blocking uncoupled light to other devices within the absorption cross-section. Accordingly the invention permits an extremely light efficient, multispectral camera among other applications.

More specifically, the present invention provides an electromagnetic radiation processing device having a concentrator providing a region of fractional phase index of refraction less than one within a predefined frequency range and adapted to receive electromagnetic radiation along an axis into the region. An electromagnetic radiation resonator communicates with the concentrator to exchange electromagnetic radiation therewith and has a resonant frequency within the predefined frequency range.

It is thus a feature of at least one embodiment of the invention to provide a method of increasing the absorption cross-section of resonators without the drawbacks of conventional lens systems and the like.

The electromagnetic radiation resonator may have a resonant frequency of $\lambda_0$ and the absorption cross-section of the electromagnetic radiation resonator may be modified by the concentrator of greater than $20\lambda_0^2/4\pi$.

It is thus a feature of at least one embodiment of the invention to provide an absorption cross-section particularly for nanoresonators that is larger than the expected optical cross-section limit.

The electromagnetic radiation may be light and the electromagnetic radiation resonator may be selected from the group consisting of an optical cavity, a quantum dot, and a fluorescent dye molecule.

It is thus a feature of at least one embodiment of the invention to provide a system broadly applicable not only to cavity-type resonators but other devices providing for energy resonance with possible stages of energy type conversion.

The electromagnetic radiation resonator may have a resonant wavelength of less than 10 micrometers It is thus a feature of at least one embodiment of the invention to provide a method of greatly increasing the absorption cross-section of extremely small structures not effectively dealt with using lens type systems.

The electromagnetic radiation resonator may be a photosensitive electrical device providing an electrical signal as a function of received light.

It is thus a feature of at least one embodiment of the invention to provide an improved light sensor for use in cameras or similar devices.

The electromagnetic radiation processing device may include multiple arrayed electromagnetic radiation resonators having different resonant frequencies within the predefined frequency range and may further include addressing circuitry for measuring electrical signals independently from each of the electromagnetic radiation resonators.

It is thus a feature of at least one embodiment of the invention to provide a multispectral detector that can increase the absorption of individual detector elements without interference with the absorption of adjacent detector elements of different frequencies. The use of a fractional phase index of refraction material allows such frequency dependent energy separation increasing the efficiency of such detector systems.

The concentrator may provide a volumetric region flanked by parallel reflectors within the predefined frequency range.

It is thus a feature of at least one embodiment of the invention to instruct a practical fractional phase index of refraction material particularly suitable for small devices.

Light received by the region may pass through a first of the parallel reflectors having a reflectance of greater than 80 percent.

It is thus a feature of at least one embodiment of the invention to provide a method of coupling energy into the concentrator in a low lost manner consistent with the desire for increasing the absorption cross-section. A reflective barrier provides an essentially lossless transition into the concentrator region.

The reflectors may be separated by one half of a wavelength within the predefined frequency range. It is thus a feature of at least one embodiment of the invention to produce an effective fractional phase index of refraction through a simple spacing of opposed reflectors.

At least one reflector may be a Bragg reflector.

It is thus a feature of at least one embodiment of the invention to provide a simple design that can be manufactured at microscopic scales using integrated circuit techniques.

The electromagnetic processing device may further include a light source providing light within the predefined frequency range directed into the region of the concentrator and an imaging photodetector positioned with respect to the region of the concentrator to receive light therefrom to provide an image of the at least one electromagnetic radiation resonator within the region.

It is thus a feature of at least one embodiment of the invention to provide a microscope system using the present invention to increase the sensitivity of detection of small resonators.

The invention may further include biological tissue having the electromagnetic radiation resonator incorporated into the biological tissue.

It is thus a feature of at least one embodiment of the invention to provide a system for using nanoresonators as taggants for medical conditions and increase the sensitivity of detection of the taggants as preferentially accumulated within certain tissue types.

These particular objects and advantages may apply to only some embodiments falling within the claims and thus do not define the scope of the invention.

BRIEF DESCRIPTION OF THE DRAWINGS

FIG. 4 is a diagram of the present invention used in a microscope for sensitive detection of nanoscale resonators used as taggants in tissue or the like;

DETAILED DESCRIPTION OF THE PREFERRED EMBODIMENT

Figure 1:
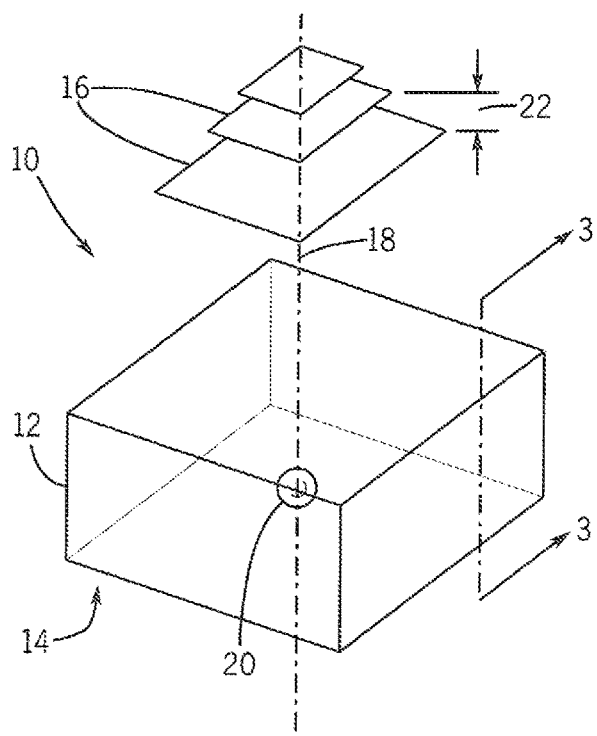
FIG. 1 is a simplified block diagram showing a resonator receiving electromagnetic radiation through a concentrator of near zero phase index of refraction per the present invention.

Referring now to FIG. 1 an electromagnetic radiation processing device 10 of the present invention may provide for a concentrator 12 defining a region 14 (in this case a rectangular volume) receiving electromagnetic radiation 16 along a reception axis 18 to pass through the region 14. Coupled to the region 14 to receive radiation from the region 14 is at least one resonator 20 providing a resonant system having a resonant wavelength $\lambda_0$ that can couple to a wavelength 22 of the electromagnetic radiation 16. In one embodiment, the resonator 20 may be within the region 14.

In systems of interest, the electromagnetic radiation 16 will include frequencies in the range that include the frequency of wavelength $\lambda_0$.

The resonator 20 may be a simple cavity resonator having one or more dimensions equal to $\lambda_0/2n$ or an integer multiple thereof and n is the index of refraction of the resonator material. Alternatively, the resonator 20 may be a system that can provide comparable resonant-like interaction with the electromagnetic radiation 16 to absorb electromagnetic radiation 16 at a resonant frequency of wavelength $\lambda_0$. Such a resonant-like interaction, for example, may be provided by quantum dots or fluorescent dye molecules or the like in which the energy reinforcement includes transfers of energy out of and into electromagnetic radiation to other energy forms, for example, electron energy elevation and the like. In one embodiment, the cavity resonator may be a homogenous material having dimensions providing the necessary boundary conditions at its index of refraction for resonance at $\lambda_0$. Such a resonator may be an inclusion of a given index of refraction material within a matrix of different indexes of refraction.

The resonators 20 may have at least one physical dimension of less than 1000 nanometers but as will be described may have an absorption cross-section of greater than 20,000 nanometers, in one example.

The concentrator 12 provides a region 14 exhibiting an effective phase index of refraction of less than one (e.g., fractional) and ideally approaching zero. Phase index of refraction refers to the apparent phase velocity of the electromagnetic radiation and not its actual group velocity and for this reason is not constrained to values greater than or equal to one as is the case with the group index of refraction. More generally, phase index of refraction can be a fraction of the group phase index of refraction. As is understood in the art, index of refraction refers to a fraction of a velocity of light (phase or group) in a vacuum as the numerator and the velocity of light in the given material whose index is being measured as a denominator. Practically, the phase index of refraction of the concentrator 12 can be less than one, preferably less than 0.5 and desirably less than 0.1 in the present invention as will be discussed below. In contrast, the group index of refraction will be one or greater.

Construction of the concentrator 12 may take advantage of a wide variety of techniques generally associated with the fabrication of metamaterials. Example techniques are described in "Dirac cones induced by accidental degeneracy in photonic crystals and zero-refractive-index materials" by Xueqin Huang, Yun Lail, Zhi Hong Hang, Huihuo Zheng, and C. T. Chan, Nature Material, Vol 10, August 2011 published online: 29 May 2011|DOI: 10.1038/NMAT3030, as well as "Realization of an all-dielectric zero-index optical metamaterial" by Parikshit Moitral, Yuanmu Yang, Zachary Anderson, Ivan I. Kravchenko, Dayrl P. Briggs and Jason Valentine, Nature Photonics, Vol 7, October 2013, published online: 25 Aug. 2013, DOI: 10.1038/NPHOTON.2013.214, as well as "Experimental realization of an epsilon-near-zero metamaterial at visible wavelengths" by Ruben Maas, James Parsons, Nader Engheta and Albert Polman, Nature Photonics, Vol 7, November 2013, published online: 13 Oct. 2013, DOI: 10.1038/NPHOTON.2013.256, all hereby incorporated by reference.

Figure 2A:
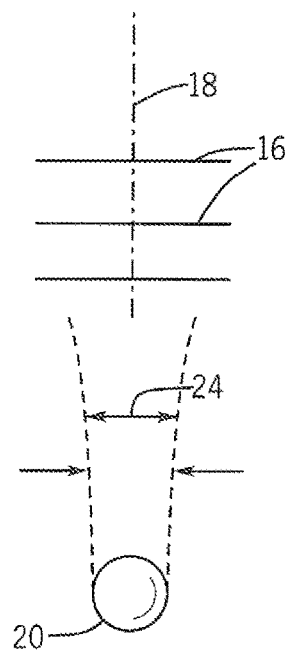
FIGS. 2a and 2b are devotional cross-sectional views of the resonator of FIG. 1 positioned with and without the concentrator of FIG. 1 showing the increase in radiation coupling area provided by the concentrator.
Figure 2B:
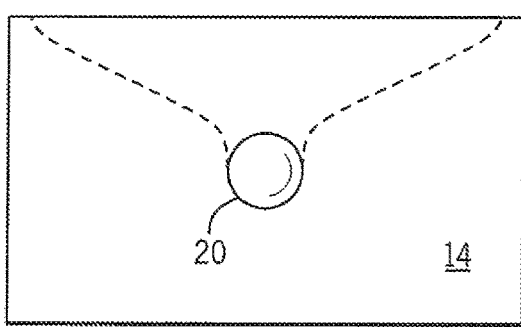

Referring now to FIG. 2a, by way of example, a resonator 20 outside of the region 14 receiving the electromagnetic radiation 16 along axis 18 will generally only couple to a electromagnetic radiation 16 within very narrow absorption cross-section 24 related to the resonant waveform of the resonator 20 according to equation (1) described above. In contrast, and referring to FIG. 2b, when the resonator 20 receives radiation through the region 14, the absorption cross-section 24 is a greatly expanded, for example, for a nanoscale optical resonator, to values greater than $10\sigma_0$ and practically greater than $20\sigma_0$, or greater than $100\sigma_0$. Simulations suggest that values of over $1000\sigma_0$ may be possible.

Figure 3:
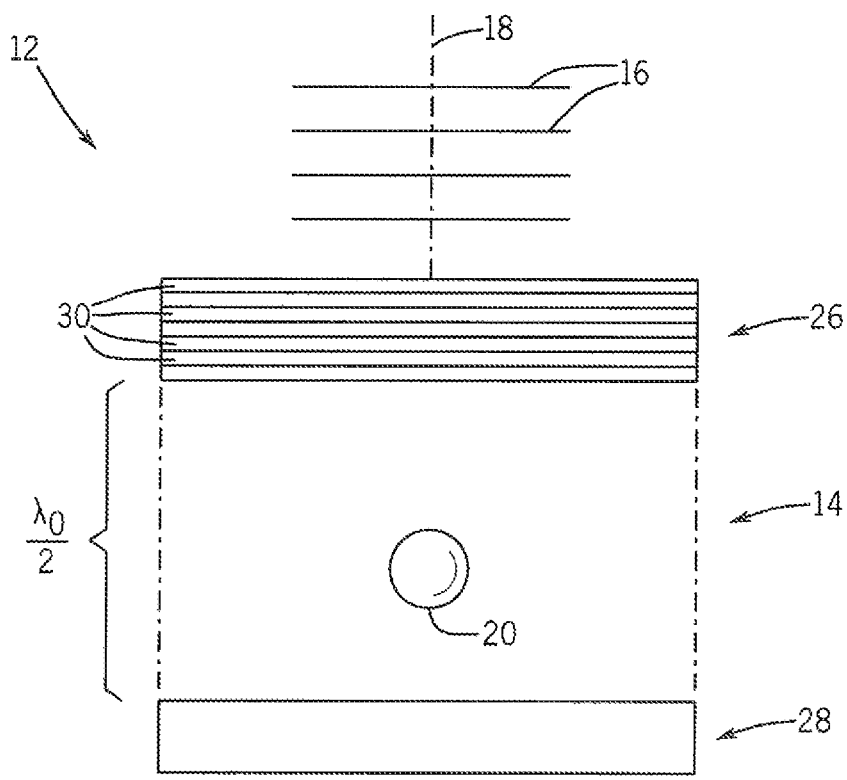
FIG. 3 is a cross-sectional view along line 3-3 of FIG. 1 showing an implementation of the concentrator using a mirror cavity.

Referring now to FIG. 3, in one embodiment, the resonator 20 may be placed between inwardly reflective mirror elements 26 and 28 positioned in parallel separation about the region 14 by a separation distance along axis 18 of $\lambda_0/2$. The mirror elements 26 and 28 extend in planes perpendicular to axis 18. The electromagnetic radiation 16 is received along axis 18 through mirror element 26 which has a reflectance of less than 100 percent, being in some embodiments greater than 75 percent, in some embodiments greater than 80 percent and preferably in some circumstances greater than 95 percent. Light passing through mirror element 26 extends into region 14 to interact with resonators 20 (as shown generally in FIG. 2b) and to be reflected back toward mirror elements 26 by mirror element 28. Mirror element 28 may desirably have a higher degree of reflectance than the mirror element 26 and will typically have a reflectance greater than 95 percent and is close to 100 percent as practical.

Mirror elements 26 and 28 may, for example, be dielectric mirrors or Bragg reflectors comprised of alternating layers 30 of materials having different group indices of refraction (for example, from alternating layers of silicon and silicon dioxide) to promote reflection at the interface of the layers. Each layer 30 provides a phase shift of after reflection of one wavelength so that constructive interference with the incident and reflected light occurs at the layer boundaries. The degree of reflectance can be readily controlled as is understood in the art (for example, by controlling the number of layers) as well as the frequencies of reflectance (for example, by controlling the layer thicknesses) which in the present invention includes the resonant wavelength of the resonator 20 of $\lambda_0$.

Figure 4:
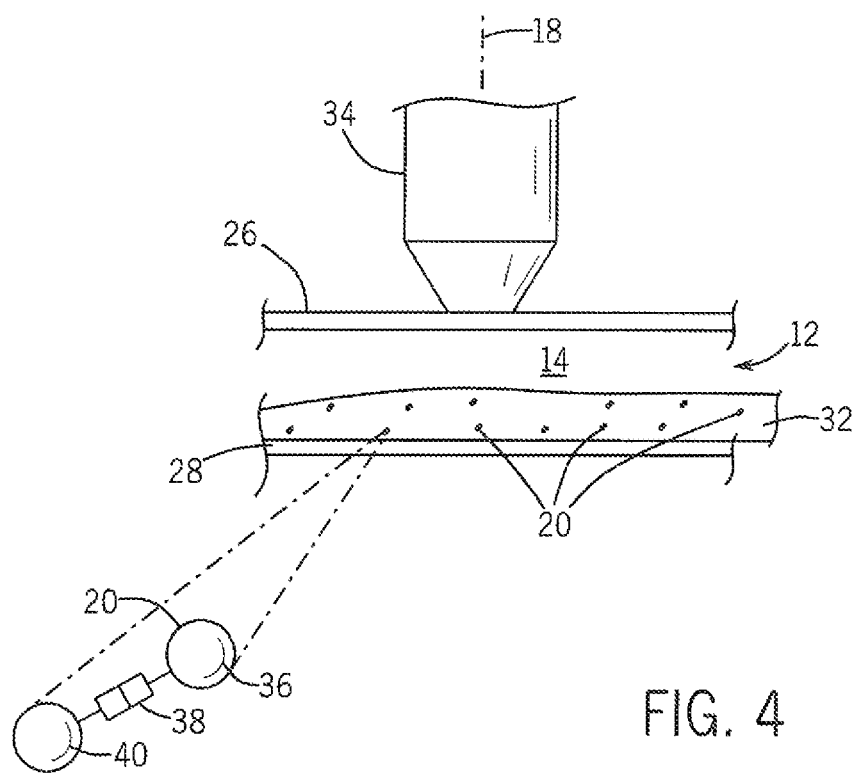

Referring now to FIG. 4, in one application, the resonators 20 may be dispersed within a biological sample such as human tissue 32. The tissue 32 may be placed in the region 14 of the concentrator 12 to receive light through the region 14, for example, as transmitted from a microscope objective 34 positioned above but adjacent to mirror element 26 to provide illumination projecting downward along axis 18 from the microscope objective 34. Light from the tissue 32 and from the embedded resonators 20 may then pass upward through mirror element 26 to be received by the microscope objective for imaging.

Each of the resonators 20, for example, may be a taggant 36, for example, a fluorescent molecule (chromophore or flurophore) or a quantum dot or the like typically married to a macromolecule 38 that may bind to tissue 32 at locations of interest or that may follow a desired metabolic pathway or the like through the tissue to accumulate in regions of interest. Here the concentrator 12 greatly increases the coupling of the resonators 20 (which are necessarily small to fulfill their tagging purpose) providing greater absorption and hence detectability. It will be appreciated that light may alternatively be provided through the lower mirror element 28 (with appropriately adjusted reflectance) so that the tissue 32 may be backlit.

Figure 5:
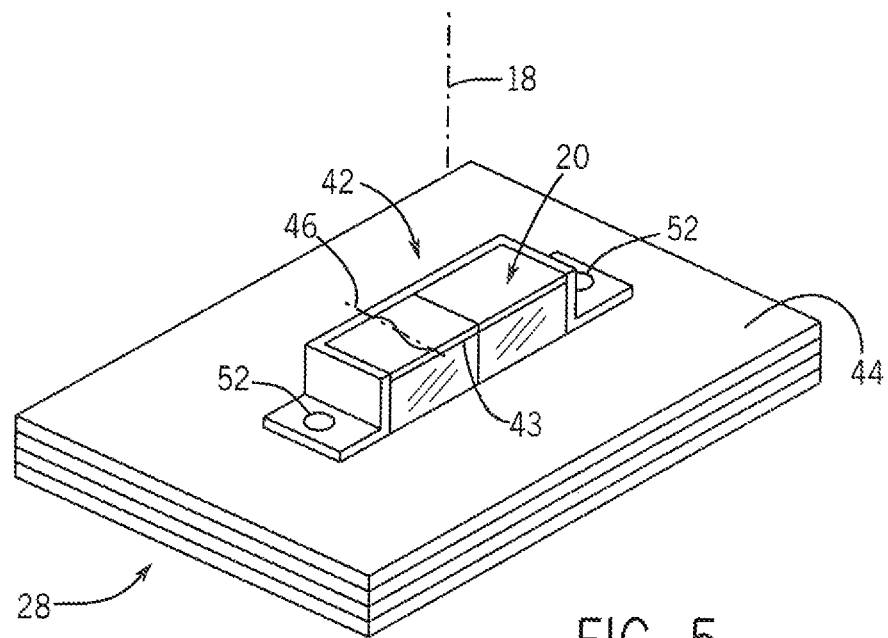
FIG. 5 is a perspective view of a photodetecting sensor used as a resonator for construction of an imaging device.
Figure 6:
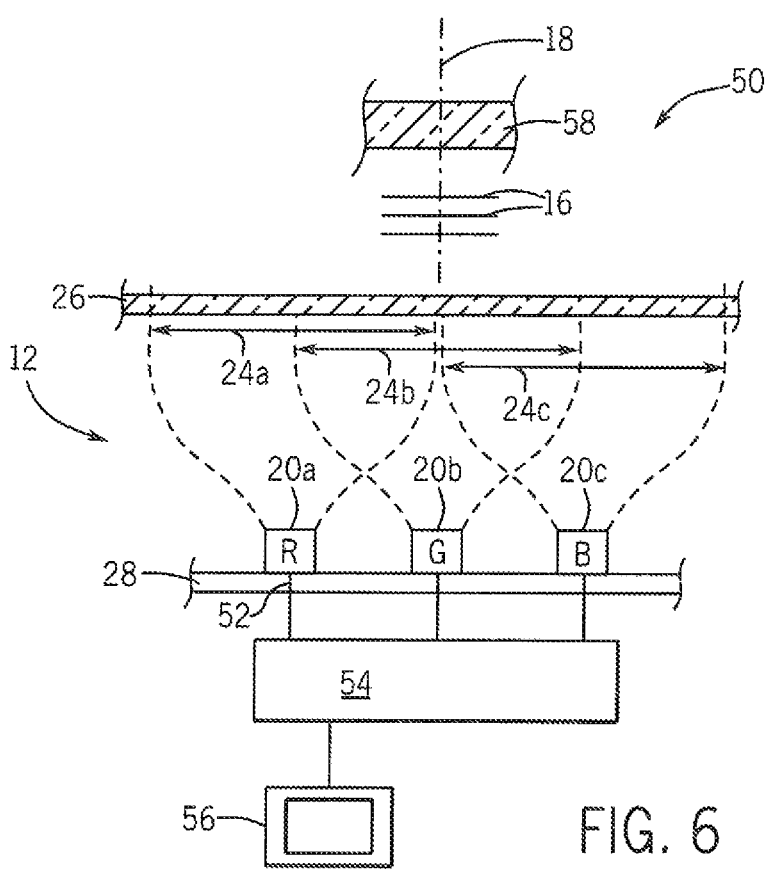
FIG. 6 is a simplified block diagram of a camera constructed using multiple tuned resonators of FIG. 5 showing energy sharing.

Referring now to FIGS. 5 and 6, in an alternative embodiment, resonators 20 may be photosensors such as a PN doped photodiode 42 arrayed along the upper surface 44 of mirror element 28. Such photodiodes 42 may be formed using integrated circuit techniques, for example, by doping and etching away semiconductor material applied to the surface of a Bragg reflector substrate, the latter also produced by integrated circuit techniques. With the material surrounding the photodiode 42 etched away to reveal the Bragg reflector mirror element 28, the photodiode 42 may provide for a resonator 20, the change in index of refraction at its lateral boundaries (for example, as coated with a higher index of refraction material 43) providing the necessary boundary conditions to produce an optical resonant cavity along at least one axis 46 with a resonant wavelength $\lambda_0$. The resulting resonator 20 receives light along axis 18 and converts it to an electrical signal in the manner of a conventional photodiode or phototransistor.

Referring specifically to FIG. 6, a multispectral photodetection imager 50, such as a camera, can be constructed in this manner. When such a multispectral photodetection imager 50 operates in the visible light range, it may provide for resonators 20a, 20b, and 20c having respective resonant wavelengths in the red, green, and blue optical region, for example. Each of the resonators 20 is positioned in region 14 of concentrator 12 so that the absorption cross-sections of each resonator 20 will be expanded to absorption cross-section 24a, 24b, and 24c exhibiting the increase discussed above with respect to FIG. 2b. Importantly, these absorption cross-sections 24, which define a coupling between the electromagnetic radiation 16 within the absorption cross-section 24 and the associated resonator 20, are not exclusive to a single resonator 20 but rather overlap as depicted reflecting the fact that these absorption cross-sections 24 define a coupling area for energy not an exclusive path of energy to a single resonator. Thus, for example, energy that does not couple into resonator 20b from absorption cross-section 24b (for example, because of a frequency mismatch) that is also within the absorption cross-section 24a is still available to couple into the resonator 20a.

As a result, greater efficiency in the light gathering power of the resonators 20 is provided by allowing sharing of absorption cross-sections 24 beyond that possible if absorption were limited to the cross-sections of the resonators 20 themselves.

Each of the resonators 20 may communicate, for example, by electrical vias 52, through the mirror element 28 to an addressing circuit allowing independent measurement of the electrical signal of each of the resonators 20. The addressing circuit 54 may be a conventional active pixel addressing system or a charge-coupled device addressing system or the like as is generally understood in the art. Image data may then be provided to a display 56, for example, or recorded or the like. A conventional optical system 58 (such as conventional lenses) may be positioned above mirror element 26 to provide light imaging on the surface defined by the resonators 20.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in then entireties.

The invention claimed is:

1. An electromagnetic radiation processing device comprising:
   an illumination source producing light having a light frequency;
   a concentrator receiving the light and providing a region of fractional phase index of refraction less than one within a predefined frequency range arid adapted to receive electromagnetic radiation along an axis into the region; and
   at least one electromagnetic radiation resonant at the light frequency and communicating with the concentrator to exchange electromagnetic radiation therewith and having a resonant frequency within the predefined frequency range.

2. The electromagnetic radiation processing device of claim 1 wherein the fractional phase index of refraction of the concentrator is less than 0.5 within the predefined frequency range.

3. The electromagnetic radiation processing device of claim 1 wherein the electromagnetic radiation resonator has a resonant frequency of $\lambda 0$ and wherein the absorption cross-section of the electromagnetic radiation resonator is modified by the concentrator of greater than $20\lambda_0^2/4\pi$.

4. The electromagnetic radiation processing device of claim 1 wherein the electromagnetic radiation is light and the electromagnetic radiation resonator is selected from the group consisting of an optical cavity, a quantum dot, and a fluorescent dye molecule.

5. The electromagnetic radiation processing device of claim 1 wherein the electromagnetic radiation resonator has a resonant wavelength of less than 10 micrometers.

6. The electromagnetic radiation processing device of claim 1 wherein the electromagnetic radiation resonator is a photosensitive electrical device outputting an electrical signal as a function of received light.

7. The electromagnetic radiation processing device of claim 6 including multiple arrayed electromagnetic radiation resonators having different resonant frequencies within the predefined frequency range.

8. The electromagnetic radiation processing device of claim 7 further including addressing circuitry for measuring electrical signals independently from each of the electromagnetic radiation resonators.

9. An electromagnetic radiation processing device comprising:
   a concentrator providing a region of fractional phase index of refraction less than one within a predefined frequency range and adapted to receive electromagnetic radiation along an axis into the region; and
   at least one electromagnetic radiation resonator resonant at the light frequency and communicating with the concentrator to exchange electromagnetic radiation therewith and having a resonant frequency within the predefined frequency range
   wherein the concentrator provides a volumetric region flanked by parallel reflectors within the predefined frequency range.

10. The electromagnetic radiation processing device of claim 9 wherein light received by the region passes through a first of the parallel reflectors having a reflectance of greater than 80 percent.

11. The electromagnetic radiation processing device of claim 10 wherein the reflectors are separated by one half of a wavelength within the predefined frequency range.

12. The electromagnetic radiation processing device of claim 9 wherein at least one reflector is a Bragg reflector.

13. The electromagnetic radiation processing device of claim 1 wherein the electromagnetic radiation resonator is within the region.

14. The electromagnetic radiation processing device of claim 1 further including a light source providing light within the predefined frequency range directed into the region of the concentrator and an imaging photodetector positioned with respect to the region of the concentrator to receive light there from to provide an image of the at least one electromagnetic radiation resonator within the region.

15. The electromagnetic radiation processing device of claim 14 further including biological tissue wherein the electromagnetic radiation resonator is incorporated into the biological tissue.

16. A method of multispectral imaging comprising the steps of:
   preparing a set of electromagnetic radiation resonators having different resonant wavelengths;
   placing the set of electromagnetic radiation resonators outputting electric signals as a function of received light and positioned within a concentrator providing a region of fractional phase index of refraction within a predetermined frequency range and adapted to receive electromagnetic radiation along an axis into the region, the predetermined frequency range including frequencies of the different resonant wavelengths;
   independently sensing electromagnetic radiation absorbed by the resonators using an addressing system for addressing the electrical signals from the electromagnetic radiation resonators to output image data.

17. The method of claim 16 further including the step of generating an image from the independently sensed electromagnetic radiation absorbed by the resonators.

* * * * *